(12) United States Patent
Seidman

(10) Patent No.: US 6,933,120 B2
(45) Date of Patent: Aug. 23, 2005

(54) METHOD OF DETERMINING BIOLOGICAL/MOLECULAR AGE

(76) Inventor: Michael D. Seidman, 5310 Putman, West Bloomfield, MI (US) 48323

( * ) Notice: Subject to any disclaimer, the term of this patent is extended or adjusted under 35 U.S.C. 154(b) by 0 days.

(21) Appl. No.: 10/271,469

(22) Filed: Oct. 15, 2002

(65) Prior Publication Data

US 2003/0092052 A1 May 15, 2003

Related U.S. Application Data

(63) Continuation-in-part of application No. 09/885,732, filed on Jun. 20, 2001, now abandoned.
(60) Provisional application No. 60/212,747, filed on Jun. 20, 2000.

(51) Int. Cl.[7] ........................... C12Q 1/68; C12P 19/34; C07K 1/00
(52) U.S. Cl. ........................... 435/6; 435/91.2; 530/350
(58) Field of Search ................. 435/6, 91.2; 536/24.33, 536/23.1; 530/350

(56) References Cited

U.S. PATENT DOCUMENTS 6,280,966 B1 * 8/2001 Anderson et al. .............. 435/6
6,322,974 B1 * 11/2001 Runge et al. .................. 435/6

OTHER PUBLICATIONS

Rotig et al. Deletion of mitochondrial DNA in a case of early–onset diabetes mellitus, optic atrophy, and deafness (wolfram syndrome, MIM 222300). J Clin Invest., vol. 91, pp. 1095–1098, 1993.*
Wei et al. Oxidative damage and mutation to mitochondrial DNA and age–dependent decline of mitochondrial respiratory function. Ann. N.Y.A.Sci., vol. 854, p. 155–170, 1998.*
Liu et al. Smoking–associated mitochondrial DNA mutations in human hair follicles. Environmental and Molecular Mutagenesis, vol. 30, p. 47–55, 1997.*
Bai et al. Mitochondrial DNA deletions associated with aging and possibly Presbycuss: A human archival temporal Bone study. Am. J. Otology, vol. 18(4) pp. 449–453, 1997.*
Lezza et al. Correlation between mitochondrial DNA 4977–bP deletions and repiratory chain enzyme activities maging human skeletal muscles. Biochem. Biophy. Res. comm., vol. 205 No. 1, pp. 272–279, 1994.*
Fahn et al. Smoking–associated mitochondiral DNA mutations and Gpral Peroxidation in human lung tissues. Am. J. Respir. Cell. Mol. Biol., vol. 19, pp. 901–909, 1998.*
Wei et al. Oxidative damage and mutations to mitochondrial DNA and age–dependent decline of mitochondiral respiratory function. Am. N. A. Sci., vol. 854, pp. 155–170, 1998.*
Biochimica et Biophyscia Acta 1226 (1994) 37–43; Hsin–Chen Lee, et al Differential accumulations of 4,977 bp deletion in mitochondrial DNA of various tissues in human ageing.
Mutation Research, 275 (1992) 181–193 M.N. Gadaleta, et al Mitochondrial DNA copy number and mitochondrial DNA deletion in adult and senescent rats.

American Journal of Respiratory and Critical Care Medicine, vol. 154 (1996) pp. 1141–1145 Huei–Jyh Fahn, et al Aged–related 4,977 bp Deletion in Human Lung Mitochondrial DNA.
Mutation Research, 316 (1994) 69–78 Wade Edris, et al Detection and quantitation by competitive PCR of an age–associated increase in a 4.8–kb deletion in rat mitochondrial DNA.
Mutation Research, 275 (1992) 169–180 M. Corral–Debrinski, et al Association of mitochondrial DNA damage with aging and coronary atherosclerotic heart disease.
Am.J.Hum.Genet. 54:618–630, 1994 Allesandra Baumer, et al Age–related Human mtDNA Deletions: A Heterogeneous Set of Deletions Arising at a Single Pair of Directly Repeated Sequences.
Biochemical and Biophysical Research Communications, vol. 205, No. 1, 1994; Nov. 30, 1994; pp. 772–779 A.M.S. Lezza, et al Correlation Between Mitochondrial DNA 4977–bp Deletion and Respiratory Chain Enzyme Activities in Aging Human Skeletal Muscles.
Laryngoscope, vol. 106, No. 6, Jun. 1996 Michael D. Seidman, M.D., et al Association of Mitochondrial DNA Deletions and Cochlear Pathology: A Molecular Biologic Tool.
Archives of Otolaryngol—Head & Neck Surgery, vol. 123, Oct. 1997; pp. 1039–1944 Michael D. Seidman, M.D., et al Mitochondrial DNA Deletions Associated With Aging and Presbyacusis.
The American Journal of Otology, vol. 21, No. 2 (2000); pp. 161–167 Michael D. Seidman, et al Biologic Activity of Mitochondrial Metabolites on Aging and Age–Related Hearing Loss.
The Laryngoscope 110: May 2000; pp. 727–738 Michael D. Seidman, M.D. Effects of Dietary Restriction and Antioxidants on Presbyacusis.
Hearing Research 154 (2001) 73–80 Uma Bai, et al A specific mitochondrial DNA deletion (mtDNA 4977) is identified in a pedigree of a family with hearing loss.
The American Journal of Otology, vol. 18, No. 4, 1997, pp. 449–453 Uma Bai et al Mitochondrial DNA Deletions Associated With Aging Possibly Presbycusis: A Human Archival Temporal Bone Study.
The Journal of the American Medical Association, Oct. 2, 1991, vol. 266, No. 13, pp. 1812–1816 Marisol Corral–Debrinski, Ph.D., et al. Hypoxemia Is Associated With Mitochondrial DNA Damage and Gene Induction—Implications for Cardiac Disease.

(Continued)

Primary Examiner—Jeffrey Fredman
Assistant Examiner—Suryaprabha Chunduru
(74) Attorney, Agent, or Firm—Gifford, Krass, Groh, Sprinkle, Anderson & Citkowski, P.C.

(57) ABSTRACT

Methods of obtaining a measurement indicative of oxidative stress and the molecular age of an individual include the step of detecting a mitochondrial DNA deletion and correlating the quantity of the deletion with a measurement of a parameter related to oxygen metabolism.

8 Claims, No Drawings

OTHER PUBLICATIONS

The Laryngoscope 108: Apr. 1998; pp. 580–584 Narihisa Ueda, M.D., et al. Mitochondrial DNA Deletion Is a Predisposing Cause for Sensorineural Hearing Loss.

The Journal of Biological Chemistry, vol. 270, No. 42, Oct. 20, 1995; pp. 24769–24775 Susan M. Tanhauser, et al Multiple Deletions are Detectable in Mitochondrial DNA of Aging Mice.

The Laryngoscope 110: Dec. 2000; pp. 2123–2127 Jose M. Manaligod, M.D., et al. Age–Related Mitochondrial DNA Mutations in the Human Larynx.

Seidman MD et al. Association of Mitochondrial DNA deletions and Cochlear Pathology: A molecular biologic tool. Laryngoscope 106: 777–783, 1996.

Corral–Debrinski M et al. Association of mitochondrial DNA damage with aging and coronary atheroscerotic heart disease. Mutation Research, 275: 169–180, 1992.

Lee HC et al. Differential accumulations of 4,977 bp deletion in mitochondrial DNA of various tissues in human ageing. Biochimica et Biophyysica Acta., 1226: 37–43, 1994.

* cited by examiner

SEQUENCE LISTING

```
<160> NUMBER OF SEQ ID NOS: 3
<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
aggcgctatc accactcttg ttcg                                              24

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
aacctgtgag gaaaggtatt cctgc                                             25

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gaattcccct aaaaatcttt gaaat                                             25
```

METHOD OF DETERMINING BIOLOGICAL/MOLECULAR AGE

RELATED APPLICATIONS

This application is a continuation-in-part of U.S. patent application Ser. No. 09/885,732 filed Jun. 20, 2001 now abandoned, which claims priority of U.S. Provisional Patent Application Ser. No. 60/212,747 filed Jun. 20, 2000, which are incorporated herein by reference.

SEQUENCE LISTING

This application contains a Sequence Listing that is being submitted herewith as a separate document.

FIELD OF THE INVENTION

The present invention relates to physiological measurements indicative of fitness and aging. In particular, the invention relates to a method of obtaining a measurement indicative of oxidative stress in an individual. This invention relates to a method of determining the biological/molecular age of a human and more particularly to such a method which involves detection of and quantification of aging deletions and comparison of the quantified deletions with known normative data.

BACKGROUND OF THE INVENTION

Aging is a complex process that involves metabolic and physiologic changes that lead to an increasing susceptibility to disease and ultimately death. In order to address the basis for this patent, an explanation of several of the major scientific hypotheses explaining aging will be discussed. There are many theories to explain the aging process. However, three leading theories have the greatest scientific support and include: the membrane hypothesis of aging (MHA), the telomerase theory of aging, and the dysdifferentiation hypothesis of aging.

The membrane hypothesis of aging (MHA), also called the mitochondrial clock theory of aging, is based upon the progressive accumulation of oxidative damage and is directly related to this patent. This progressive damage occurs secondary to the action of reactive oxygen species (ROS) also known as free radicals which are generated in increasing quantities with age.[1,2] ROS are known to damage DNA in general and mitochondrial DNA in specific, as well as cells and tissue. The mitochondrial DNA damage leads to reduced capacity for energy generation within the mitochondria and ultimately causes aging and death. This is the premise for the use of powerful antioxidants to perhaps slow the processes of aging.

The mitochondrion is a tiny structure inside a cell and is the primary generator of energy, in the form of adenosine tri-phosphate (ATP). Mitochondria have their own DNA which determines all of their functions. The mitochondrial DNA (mtDNA) is made up of 16569 base pairs that, when completely intact, makes energy for the body. However, subtle changes in the MtDNA have dramatic effects on mitochondrial function and energy production. Research in our laboratory, and in several others around the world, has identified a specific deletion (or elimination) in mitochondrial DNA that is known to occur in response to aging. It is called the common aging deletion and consists of 4977 base pairs. There are other MtDNA deletions that can occur in response to aging, such as the 520 bp deletion, etc. It is not difficult to comprehend that if you remove approximately one-third of the mitochondrial DNA you will have significant problems with energy generation. It has been found that even minor amounts of this deletion severely alter energy production and cellular function.

Studies have demonstrated an age-dependent increase in the presence of the common mitochondrial deletion ($MtDNA^{4977}$ in human; $MtDNA^{4834}$ in rat).[3] Specifically, the common aging deletion was identified in one of fifteen young rats, while eleven of fourteen aged rats had the MtDNA deletion. The aged rats also had hearing loss, and even more interesting is that the three aged rats without the deletion had better hearing when compared to the eleven with the deletion. Additionally, we were able to study mitochondrial function in aged rats and humans, it is significantly reduced compared to the young subjects. Human studies have revealed the presence of this MtDNA deletion in white blood cells of patients with age-related hearing loss more often than in control patients.[4] Two other human studies have identified the common aging deletion ($MtDNA^{4977}$) in patients with age-related hearing loss more than in control subjects.[5,6]

It is proposed to use this sensitive molecular biologic test to study MtDNA deletions and determine, with accuracy, an individual's "molecular age". Preliminary evidence and logic predicts that even though two people may have the same chronologic age, that due to variations in lifestyle, diet, socio-economic factors and genetics, their molecular age may well be very different. For example: There are two forty year old men: One lives in Northern Michigan (at sea level) has an excellent diet, exercises regularly, supplements with specific nutrients, doesn't smoke or spend much time in the sun. Additionally, this Michigan native has a body mass index of 22 (normal=<25). Contrast this to another 40 year old man who lives in Colorado (about 5000 feet above sea level, this provides for more ionizing radiation), has a poor diet, rarely exercises, doesn't use nutritional supplements, smokes a half pack of cigarettes per day and is always out in the sun. Additionally, his BMI is 32 (considered obese). Even though both are 40 years old, analysis of their mitochondria shows vast differences with 10–200 fold increases in the MtDNA deletion in the gentleman from Colorado. In essence, the man from Colorado has more rapid aging and in reality has the mitochondria of a 65 year old. This information is a wakeup call to alter one's lifestyle immediately. This test provides critical information regarding one's molecular age and an indirect measure of long-term ROS damage.

It is known that certain tissues are more susceptible to oxidative damage (damage from free radicals) and reduced energy supply. This is particularly true for tissues that no longer make new cells. For example, brain, eye, inner ear, and all muscle can accumulate high amounts of these deletions and they become more susceptible to free radical damage than other tissues. Thus, increased oxidative damage that is associated with aging preferentially affects these tissues.

There are two other leading theories of aging: (1) the telomerase theory of aging and (2) the dysdifferentiation theory of aging. The end of a chromosome is made up of a structure called the telosome. The tip of the telosome is a region of repeating DNA sequences and proteins called the telomere. The telomerase theory of aging suggests that there is a reduction in telomere length over time.[7] Another way to look at this is to consider the telosome as similar to the tail of a rattlesnake. There are a finite number of rings on a telosome (or a rattlesnake) and the theory suggests that each time the telosome reproduces one ring is lost. When there are only a few rings of the telosome left, death is imminent.

Interestingly, the activation of the enzyme responsible for making these rings disappear (telomerase enzyme) can be manipulated experimentally. However, it has already been found that cancer alters the telomerase enzyme, thereby becoming immortal. It is felt that special genes, called viral oncogenes, may produce immortality of a cell or tissue by activating telomerase, thus effectively preventing telomere shortening and sustaining cellular growth of tumors.[8] Although many aspects of telomerase activity remain undefined, it has been hypothesized that the balance between telomere shortening and telomerase activity may underlie cellular aging processes. Furthermore, caution must be exercised when these genes are manipulated, because of the potential to trigger cancerous change.

The dysdifferentiation hypothesis suggests that there is a preprogrammed activation of genes that are deleterious to the cell and lead to activation of enzymes and reactions that are responsible for age-related changes. This line of reasoning was, in part, brought to the forefront from work elaborating control mechanisms of aging in the earthworm. Two main genes, Bax and BCl2, have essential roles in cellular aging and immortality respectively. Scientists were able to increase the lifespan of the common earthworm by 30–40% by increasing the activity of the BCl2 gene. However, once again, it has been shown that several cancers become immortal precisely by up-regulating the BCl2 gene.

The process of aging is associated with many molecular, biochemical and physiological changes including increases in DNA damage, reduction in mitochondrial function, decreases in cellular water concentrations, ionic changes, and decreased elasticity of cellular membranes. One contributing factor to this process is altered vascular characteristics, such as reduced flow and vascular plasticity as well as increased vascular permeability.[9,10] Atherosclerosis and high lipids and cholesterol further affect these situations and reduce the overall blood flow to many tissues in the body. These age-related changes result in reductions in oxygen and nutrient delivery and in waste elimination.[11-14] These physiologic inefficiencies favor the production of ROS. Furthermore, there is support in the literature for age-associated reduction in enzymes that protect from ROM damage including superoxide dismutase, catalase and glutathione.[15-17] Collectively, these changes enhance the generation of ROS.

One of the most important factors in aging is the level of oxidative stress. Oxidative stress occurs when the usual balance between reactive oxygen species and antioxidants is disturbed. Each individual's level of oxidative stress is different and depends on a number of factors including fitness, genetics, disease and metabolic rate. There is a continuing need for a method to formulate a molecular age of an individual based on the individual's physiological state and level of oxidative stress in order to provide a basis and motivation for medical treatment and lifestyle change.

SUMMARY OF THE INVENTION

A method is provided for obtaining a measurement indicative of oxidative stress in an individual subject. Such a method includes the steps of obtaining a specimen from the individual and performing an assay on the specimen in order to detect a quantity of a mitochondrial DNA deletion. The quantity of the mitochondrial DNA deletion detected is compared to a reference and a first value is generated by this comparison. Additionally, a parameter related to the individual's oxygen metabolism is assessed and a second value is obtained as a result of this assessment. Then, the first and second values are correlated in order to obtain a measurement indicative of oxidative stress.

In a further method for obtaining a measurement indicative of oxidative stress in an individual subject, a specimen from an individual subject is obtained and tested in order to detect a quantity of a mitochondrial DNA deletion. The quantity of the mitochondrial DNA deletion detected is compared to a reference and a first value is generated by this comparison. Additionally, an antioxidant indicator is assayed and a second value is obtained thereby. The first and second values are correlated in order to obtain a measurement indicative of oxidative stress.

DETAILED DESCRIPTION OF A PREFERRED EMBODIMENT

Accordingly, an inventive method of obtaining a measurement indicative of oxidative stress in an individual subject is presented herein, the method including the step of obtaining a specimen from the individual subject. Mitochondrial DNA (mtDNA) is then isolated from the specimen and the mtDNA is subjected to an assay in order to detect a quantity of a deletion present therein. In a further step of an inventive method, the quantity of the deletion is compared to a reference to obtain a first value indicative of the level of an mtDNA deletion present in the specimen. In addition, an indicator related to the individual's oxygen metabolism is assessed to obtain a second value. Then, the first value and the second value are correlated over value dependant time scales to obtain a measurement indicative of oxidative stress. This information is communicated to the individual subject along with suggestions regarding treatment options and lifestyle changes.

An individual's level of oxidative stress is measured by assessing various physiological parameters related to oxygen metabolism. These data are immediate measures of metabolism. For example, such parameters include the amount of oxygen consumed, $CO_2$ produced, the ventilatory rate, a respiratory volume such as an inhalation volume or tidal volume, arterial $pO_2$, respiratory quotient and the like. Oxygen metabolism may also be estimated by measuring metabolic rate of an individual such as basal metabolic rate or resting metabolic rate. Physiological measurements relating to oxygen metabolism include the amount of reactive oxygen species, such as superoxide, which cells or tissues are exposed to. The level of reactive oxygen species is related to the amount of oxygen which a tissue or cell is exposed to and to the amount of oxygen metabolism occurring in the cell.

Further physiological parameters related to oxygen metabolism relating to oxidative stress include levels of antioxidants present in a sample obtained from an individual. An antioxidant is a substance present that inhibits oxidation of another substance. Preferably, a measured antioxidant includes those that inhibit oxidation of a substance which is a natural component of an organism, such as a lipid, a protein, a nucleic acid, or a carbohydrate, that is subject to oxidation. Exemplary antioxidants of this type include enzyme antioxidants such as superoxide dismutase, glutathione peroxidase, and catalase. Other antioxidants found naturally in an organism include tocopherols such as vitamin E, carotenoids such as beta carotene, flavonoids, glutathione, an ubiquinone such as coenzyme Q-10, and ascorbate. In another embodiment, a measured antioxidant is an antioxidant not usually found in the subject organism, such as a synthetic drug or naturally-occurring pharmaceutical substance derived from a second organism. Illustrative examples include 3,4-dihydroxybenzohydroxamic acid, 3,4,5-trihydroxybenzohydroxamidoxime and others known the art such as are found in Merck Index: An Encyclopedia of Chemicals, Drugs, & Biologicals, O'Neil et al. (Eds.), 13th edition, 2001.

An antioxidant is assayed in any cell, tissue or bodily fluid. For instance, antioxidant levels are measured in blood or fractions thereof such as plasma or serum, or other body fluids such as saliva, mucus, tears or urine. Antioxidant levels may also be measured in a cell sample from an individual including cell sources such as epidermal cells; mucosal cells; epithelial cells; hair roots; spermatozoa; and leukocytes, in particular, lymphocytes and platelets.

In a method according to the present invention, a measurement indicative of oxidative stress in an individual subject which relates to an individual's molecular age is obtained by assaying an antioxidant in a specimen obtained from the individual. An assay of an antioxidant includes assay of levels and/or the oxidation state of the particular antioxidant. For example, measurement of the ratio of reduced glutathione to oxidized glutathione is performed. Antioxidant levels are measured by techniques known in the art including any of various methods such as spectrophotometric assays, antibody-based assays such as ELISA, and activity based assay among others. For example, superoxide dismutase activity is measured by an indirect assay using a nitroblue tetrazolium. Commercial kits are available for assay of antioxidants, such as the glutathione peroxidase ELISA kit from CalBiochem. Other common antioxidants such as vitamin E and vitamin C are measured for instance, by high performance liquid chromatography or other suitable methods known in the art.

In a further step to obtain a measurement indicative of oxidative stress, an assay for mitochondrial deletions in a specimen obtained from the individual is performed. These data are representative of a time period beyond the moment of measurement. Assay of mitochondrial DNA deletions includes a step of detection of mitochondrial DNA deletions. There are a large number of mitochondrial DNA deletions that are known to occur and human deletions are well-studied. Information on the mitochondrial genome, including DNA sequence and base pair reference numbers is available, for example see reference 51. In particular, the deletion known as 4977 which occurs at nucleotide 8469 to 13447 in human mt DNA is commonly observed, for example, see references 21 and 45–48. DNA in the region of the 4977 deletion encodes NADH dehydrogenase subunit 5 and mitochondrial ATP synthase subunit 8. Further commonly observed human mitochondrial DNA deletions include a 6063 deletion occurring at nucleotide 7841 to 13905 (refs. 47, 49–50), a 7436 base pair deletion occurring at 8648 to 16085 (refs. 28–29), and other common DNA deletions such as is detailed in references 18–44 below and other references cited herein. RNA molecules transcribed and proteins encoded by the regions encompassed by the various deletions are known in the art.

Deletions are detected by, for example, molecular assays such as polymerase chain reaction (PCR), primer extension, restriction fragment length polymorphism, in situ hybridization, reverse transcription-PCR, differential display of RNA, and antibody based protein detection.

A particularly preferred method of deletion detection includes a polymerase chain reaction. PCR methods are known in the art, as are guidelines for choosing specific primers to detect specific deletions. Details of reaction protocols and parameters considered in choosing appropriate primers are found in standard references such as Sambrook et al., Molecular Cloning: A Laboratory Manual, Cold Spring Harbor Laboratory, 3$^{rd}$ Edition, 2001; Dieffenbach and Dveksler, PCR Primer: A Laboratory Manual, Cold Spring Harbor Laboratory, 1995; PCR Protocols: Current Methods and Applications (Methods in Molecular Biology, 15) by Bruce A. White (Ed.), 1993; and in the examples below.

In a further embodiment, an assay for mtDNA deletions includes an assay for protein products of mtDNA. In this assay, the level of a protein product encoded by a deleted region of mtDNA is compared with the level of another protein encoded by intact nuclear DNA or mtDNA. For example, mammalian cytochrome oxidase consists of thirteen subunits of which subunits I, II and III are encoded by mitochondrial DNA and the remaining subunits are encoded by nuclear DNA. An assay for mitochondrial DNA deletions may include assay of presence or absence of mitochondrial encoded cytochrome oxidase subunits I, II or III compared to a nuclear encoded subunit. In another example, an assay for the 4977 mtDNA deletion may include an assay of NADH dehydrogenase subunit proteins or ATP synthase subunit proteins. In this assay, levels of mtDNA encoded NADH dehydrogenase subunit 5 or mitochondrial ATP synthase subunit 8 are assayed.

A detected mitochondrial DNA deletion is preferably compared to a reference in order to provide a quantitative assessment of a mitochondrial deletion. Where the mtDNA deletion is detected by assessing a nucleic acid, a reference is preferably another nucleic acid in the specimen, such as non-deleted mitochondrial DNA, genomic DNA, mitochondrial RNA including messenger RNA, ribosomal RNA and transfer RNA, and RNA encoded by nuclear DNA, including messenger RNA, ribosomal RNA and transfer RNA. Quantitative PCR methods and standards are known in the art and are detailed in the examples below and in references such as Quantitative PCR Protocols (Methods in Molecular Medicine, Vol 26), Kochanowski and Reischl (Eds.), Humana Press; 1999. Where proteins encoded by mtDNA deletions are assayed, an appropriate protein reference, such as a nuclear encoded protein or a mitochondrial protein from a distinct region of the mitochondrial genome is assayed.

Since mitochondria exist in most cells of the body, any of various cells or tissues is used as a specimen for assay of a mitochondrial deletion. Previously, measurements of mtDNA deletions required invasive sampling or biopsy of organs such as liver and post-mitotic tissues such as brain. An inventive method allows non-invasive sampling for mtDNA deletion analysis and provides practical methods for achieving the obtention of a measure of oxidative stress. In particular, samples from an individual for use in a method according to the present invention are obtained from easily accessed material such as epidermal cells; mucosal cells, such as from the buccal or nasal cavity; epithelial cells; hair roots; spermatozoa; and blood cells such as leukocytes, in particular, lymphocytes and platelets. In addition, various bodily fluids and secretions are assayed for mitochondrial deletions in cells contained therein. For instance blood, urine, saliva, mucus and tears are sampled. In addition, different tissues are compared with each other, for instance a tissue containing cells which have relatively low turnover rates such as muscle cells might be compared with cells that are continually renewed, such as epidermal cells, in order to obtain temporal information about when deletions have occurred. In another embodiment a measurement in a sample from one cell type is compared with previous measurements from that cell type in order to obtain information on ongoing oxidative stress in the individual. Measurements of the quantity of mitochondrial DNA deletions are taken at intervals, the interval length dependent on the typical lifetime of the cell to be assayed. For instance, specimens of scalp hair including roots are taken over a period of time ranging from days to years.

Once a sample is obtained, assay for mtDNA deletions is performed on whole lysed cell preparations, isolated total nucleic acid preparations, isolated mitochondria or isolated mitochondrial nucleic acids. For assay of mitochondrial DNA deletions include preparation of total DNA from cell samples and purified mitochondrial DNA. Techniques for isolation and purification of mitochondria and various nucleic acids are known in the art. For example, various protocols are known for purification of mitochondria such as those found in Current Protocols in Cell Biology, Bonifacino, Dasso, Lippincott-Schwartz, Harford, and Yamada (Eds.), John Wiley & Sons, Inc. Further, kits for isolation of mitochondria are commercially available, for example from Sigma-Aldrich.

In a preferred method, mtDNA deletions are detected in blood cells, such as leukocytes. These cells are easily sampled, for example by a blood draw via a needle inserted into a blood vessel. Blood samples ranging in volume from 0.1 milliliter to 10 milliliters are typically used in detecting deletions, although more or less may be used. Particular populations of blood cells are optionally purified for analysis. For example, platelets are a preferred cell type for some applications since they contain mitochondria but no nucleus, facilitating assay of mtDNA. Protocols for isolation of specific populations of blood cells, including platelets, are known in the art, as are methods for purification of mitochondria, nucleic acids and proteins.

It will be appreciated that a method according to the present invention is applicable to various species, including humans, horses, cows, pigs, sheep, goats, rats, mice and avian species such as chickens. In species having organelle-containing erythrocytes, these cells are also appropriate for DNA analysis.

In a further step according to an inventive method, the measure of an oxygen related parameter and the measure of the quantity of an mtDNA deletion are related to obtain a measurement of oxidative stress in the individual. The relation of these measurements yields a significantly more informative measure of oxidative stress in an individual than either measure alone. For example, comparison of a measure of a parameter related to oxygen metabolism and the measure of the quantity of an mtDNA deletion present in an individual's blood cell sample shows a high level of the antioxidant vitamin E and a high level of an mtDNA deletion relative to levels of each usual for an individual of like age. Consideration of either measure alone yields some information regarding the health of the individual. For example, considered separately, the high level of mtDNA deletion signifies a high level of oxidative stress, indicating a need for medical intervention. A high vitamin E level represents a healthy state. Combined, these measurements not only inform the individual of various values representing aspects of oxidative metabolism, but, additionally, the combination of these measurements provides a measure that achieves a higher level of information, since the measurements represent a physiological marker of past metabolic events, a measure of actual damage done and a contemporary state of the patient's physiology in a single test. Thus, the patient and physician can effectively contemplate treatment options necessitated by the patient's molecular history and immediate molecular situation on the basis of one exam, rather than the usual basis of a series of lab test records compiled over a period of time in order to establish a history.

EXAMPLES

Example 1

Protocol

Detection and Quantification of MtDNA Deletion (MtDNA$^{4977}$)

A detailed protocol is found in reference 35, N-W Soong and N. Arnheim, *Meth Enzymol.*, 421–431, 1996.

Primers (designed in our laboratory):

```
Mt1C:                               (SEQ ID NO:1)
AGG CGC TAT CAC CAC TCT TGT TCG     (13,176-13198)

Mt2:                                (SEQ ID NO:2)
AAC CTG TGA GGA AAG GTA TTC CTG C   (13,501-13,477)

Mt1A:                               (SEQ ID NO:3)
GAA TTC CCC TAA AAA TCT TTG AAA T   (8224-8247)
```

Primers are end-labeled with ($\gamma$-$^{32}$P) ATP using T4 Polynucleotide Kinase. Unincorporated nucleotides are removed by spinning through P4 columns. These primer lots are prepared to give approximately 10× concentration for PCR (5 micromolar) and are diluted directly into the PCR mix.

Example 2

PCR Analysis

PCR is carried out in 50 microliter volumes in 1× PCR buffer, containing 1.5 mM $MgCl_2$.

$^{32}$P end-labeled primer concentration is 0.5 micromolar.

Deoxy-nucleoside triphosphate (dNTPs) 200 micromolar.

2.5 Units of Taq polymerase.

100–1000 ng of genomic DNA.

Primers for Total MtDNA: Mt1C and Mt2, fragment size 324 bp.

Primers for Deletion: Mt1A and Mt2, fragment size 303 bp.

Cycle Parameters:

Initial denaturation at 94° C. for 3 min.
Denaturation at 94° C. for 30 sec.
Annealing at 54° C. for 30 sec          } 30 cycles
Extension at 72° C. for 1 min.
Followed by 7 min extension at 72° C.

PCR conditions are identical for total and deletion-specific reactions except that deletion-specific reactions are run for 30 cycles and control PCR is carried out for 15 cycles.

Example 3

Polyacrylamide Gel Electrophoresis

After PCR, 10% (5 microliters) of each reaction is electrophoresed through 8% polyacrylamide gel. The gel is dried and counts from each specific band are quantitated with a PhosphorImager (Biorad) after 15–24 hr exposure.

Example 4

Preparation of External Standards

For the construction of standard curves for deletion and control PCR, the respective PCR products are purified as a source of templates for the amplification reactions. Genomic DNA from aged heart tissues is used as a template for these preparative PCRs. The product bands are excised, electroeluted and concentrated by centrifuging through Centricon- 10. These are aliquoted and stored at −20° C. In order to develop "normal ranges" an acceptable standard is created by studying as few as 10 people and as many as 10,000 people in each decade ranging from 0–10, 11–20, 21–30, 31–40, 41–50, 51–60, 61–70, 71–80, 81–90, 91–100, 101–110, 111–120 years etc. Individual patients are then compared to a "normal" range thus providing a range for an acceptable amount of MtDNA deletion.

Serial dilutions of external standards were made and the range of dilutions over which the amplifications were exponential was determined. The plot of log counts versus log dilutions provides a good linear fit with a slope close to 1.

Example 5

Quantitation of Samples

Preliminary deletion and control PCR with unlabeled primers are performed on dilutions of DNA samples. The products signals are visually compared in ethidium bromide stained gels along with those of generated by amplification of the most concentrated standard dilution in the exponential range. The samples can then be diluted not to exceed the exponential range of the standard.

The PCR is then repeated with $^{32}P$ labeled primers. Both control and deletion standards are amplified in parallel with the samples. The products are quantified and the signal generated by each sample is then extrapolated from the appropriate standard curve to obtain the equivalent dilution of the standard stock that would have given the same signal. The percentage of the ratio of the deletion dilution to that of control dilution would then give the % ratio of MtDNA del to total MtDNA.

Example 6

Mitochondrial DNA Deletion Analysis by Serial Dilution

A detailed protocol is found in reference 27, N. S. Hamblet and F. J. Castora, *Biochem Biophys Res Commun.*, 207:839–847, 1995.

Primers: Same as above.

PCR Reaction and Cycle Parameters: Same as above.

Protocol:

Total DNA was diluted in two ranges: one for deleted MtDNA amplification (250,000–976 pg) and one for wild type MtDNA amplification (500–1.95 pg). Samples were linearized with Bam H1 before amplification. PCR products were electrophoresed on an 8% polyacrylamide gel and visualized by ethidium bromide staining. Photographs were taken and negatives were scanned using a laser densitometer. The ratio of deleted to wild type MtDNA was determined by densitometric measurement of the intensity of each band and subsequent plotting of the optical density (OD) versus the log of weight of DNA in the reaction mix. The OD was adjusted so that the area of each DNA band was normalized by the size of the DNA fragment. The plots of deleted and wild type PCR products were examined to determine the logarithmic values on the x axis at which ODs of the deleted and undeleted PCR products were equivalent. The selected OD should be within the linear range of the density curve and has low standard deviation.

References

1. Nohl H, Hegner D. Do mitochondria produce oxygen radicals in vivo? Eur J Biochem 1978;82(2):563–567.
2. Bandy B, Davison A J. Mitochondrial mutations may increase oxidative stress: implications for carcinogenesis and aging? Free Radical Biol Med 1990;8(6):523–539.
3. Seidman et al, 1996, *Laryngoscope* 106:777–783.
4. Ueda et al. 1998, *Laryngoscope* 108:580–584.
5. Bai et al. 1997, *Am. J. Otology*, 18:449–453.
6. Fischel-Ghodsian, Mitochondrial genetics and hearing loss: the missing link between genotype and phenotype. Proc Soc Exp Biol Med. 1998 May;218(1): 1–6.
7. Pommier J P. Lebeau J. Ducray C. et al. Chromosomal instability and alteration of telomere repeat sequences. *Biochimie*. 77(10):817–25, 1995.
8. Shay J W. Wright W E. Telomerase activity in human cancer. Current opinion in oncology. 8(1):66–71, 1996 January.
9. Prazma J, Carrasco V N, Butler B, Waters G, Anderson T, Pillsbury H C. Cochlear microcirculation in young and old gerbils. Arch Otolaryngol Head Neck Surg 1990;116 (8):932–936.
10. Seidman M D, Khan M J, Dolan D F, Quirk W S. Age-related differences in cochlear microcirculation and auditory brain stem response. Arch Otolaryngol Head Neck Surg 1996; 122(11):1221–1226.
11. Gacek M R, Schuknecht H F. Pathology of presbycusis. Int Audiol 1969;8:199–209
12. Harkins S W. Effects of age and insterstimulus interval on the brainstem auditory evoked potential. Int. J Neurosci 1981;15:107–118.
13. Rosenhall U, Pederson K, Dotevall M. Effects of presbycusis and other types of hearing loss on auditory brainstem response. Scand Audiol 1986;15(4):179–185.
14. Hoeffding V, Feldman M L. Changes with age in the morphology of the cochlear nerve in rats: light microscopy. J Comp Neurol 1988;276:537–546.
15. Semsei I, Szeszek F, Nagy I. In-vivo studies of the age dependent decrease of the rates of total and mRNA synthesis in the brain cortex of rats. Arch Gerontol Geriatr 1982;1:29–42.
16. Semsei I, Roa G, Richardson A. changes in the expression of superoxide dismutase and catalase as a function of age and dietary restriction. Biochem Biophy Res Commun 1989;164(2):620–625.
17. Richard A, Butler J A, Rutherford M S, Semsei I, Gu M Z, Fernandez G, Chiang W H. Effect of age and dietary restrictions on the expression of alpha-2 $\mu$-globulin. J Biol Chem 1987;262(26):12821–12825
18. Anderson, S., Bankier, A. T., Barrell, B. G., de Bruijn, M. H., Coulson, A. R., Drouin, J., Eperon, I. C., Nierlich, D. P., Roe, B. A., Sanger, F., Schreier, P. H., Smith, A. J., Staden, R., and Young, I. G. 1981. Sequence and organization of the human mitochondrial genome. Nature 290 (5806):457–465.
19. Armheim, N. and Cortopassi, G. 1992. Deleterious mitochondrial DNA mutations accumulate in aging human tissues. Mutation Research 275:157–167.
20. Attardi, G., Chomyn, A., Montoya, J., and Ojala, D. 1982. Identification and mapping of human mitochondrial genes. Cytogenetics and Cell Genetics 32:85–98.
21. Corral-Debrinski, M., Horton, T., Lott, M. T., Shoffner, J. M., Beal, M. F., and Wallace, D. C. 1992. Mitochondrial DNA deletions in human brain: regional variability and increase with advanced age. Nature Genetics 2(4): 324–329.
22. Corral-Debrinski, M., Shoffler, J. M., Lott, M. T., and Wallace, D. C. 1992. Association of mitochondrial DNA damage with aging and coronary atherosclerotic heart disease. Mutation Research 275(3–6):169–180.
23. Corral-Debrinski, M., Stepien, G., Shoffner, J. M., Lott, M. T., Kanter, K., and Wallace, D. C. 1991. Hypoxemia is associated with mitochondrial DNA damage and gene induction. JAMA 266(13):1812–1816.
24. Cortopassi, G. and Arnheim, N. 1992. Accumulation of mitochondrial DNA mutation in normal aging brain and muscle. In Mitochondrial DNA in Human Pathology. DiMauro, S. and Wallace, D. C., Editors. Raven Press:N.Y. p. 125–136.
25. Cortopassi, G. A. and Arrheim, N. 1990. "Detection of a specific mitochondrial DNA deletion in tissues of older humans. Nucleic Acids Research 18(23):6927–6933.
26. Cortopassi, G. A., Shibata, D., Soong, N. W., and Arnheim, N. 1992. A pattern of accumulation of a somatic deletion of mitochondrial DNA in aging human tissues. Proceedings of the National Academy of Sciences of the United States of America 89(16):7370–7374.
27. Hamblet, N. S. and Castora, F. J. 1995. Mitochondrial DNA deletion analysis: a comparison of PCR quantitative methods. Biochemical and Biophysical Research Communications 207(2):839–847.
28. Hattori, K., Tanaka, M., Sugiyama, S., Obayashi, T., Ito, T., Satake, T., Hanaki, Y., Asai, J., Nagano, M., and Ozawa, T. 1991. Age-dependent increase in deleted mitochondrial DNA in the human heart: possible contributory factor to presbycardia. American Heart Journal 121(6 Pt 1):1735–1742.
29. Hayakawa, M., Sugiyama, S., Hattori, K., Takasawa, M., and Ozawa, T. 1993. Age-associated damage in mitochondrial DNA in human hearts. Molecular and Cellular Biochemistry 119(1–2):95–103.
30. Mann, V. M., Cooper, J. M., and Schapira, A. H. V. 1992. Quantitation of a mitochondrial DNA deletion in Parkinson's disease. FEBS Letters 299(3):218–222.
31. Melov, S., Shoffher, J. M., Kaufman, A., and Wallace, D. C. 1995. Marked increase in the number and variety of mitochondrial DNA rearrangements in aging human skeletal muscle [published erratum appears in Nucleic Acids Res 11 Dec. 1995;23(23):4938]. Nucleic Acids Research 23(20):4122–4126.
32. Nagley, P., Mackay, I. R., Baumer, A., Maxwell, R. J., Vaillant, F., Wang, Z. X., Zhang, C., and Linnane, A. W. 1992. Mitochondrial DNA mutation associated with aging and degenerative disease. Annals of the New York Academy of Science 673:92–102.
33. Nagley, P., Zhang, C., Martinus, R. D., Vaillant, F., and Linnane, A. 1992. Mitochondrial DNA mutation and human aging: molecular biology, bioenergetics, and redox therapy. In Mitochondrial DNA in Human Pathology. DiMauro, S. and Wallace, D. C., Editors. Raven Press:N.Y. p. 137–157.
34. Simonetti, S., Chen, X., DiMauro, S., and Schon, E. A. 1992. Accumulation of deletions in human mitochondrial DNA during normal aging: analysis by quantitative PCR. Biochimica et Biophysica Acta 1180:113–122.
35. Soong, N. W., Hinton, D. R., Cortopassi, G., and Arnheim, N. 1992. Mosaicism for a specific somatic mitochondrial DNA mutation in adult human brain. Nature Genetics 2:318–323.
36. Sugiyama, S., Hattori, K., Hayakawa, M., and Ozawa, T. 1992. Quantitative analysis of age-associated accumulation of mitochondrial DNA with deletion in human hearts. Biochemical and Biophysical Research Communications 180:894–899.
37. Wei, Y. H. 1992. Mitochondrial DNA alterations as ageing-associated molecular events. Mutation Research 275:145–155.
38. Yen, T. C., Chen, Y. S., King, K. L., Yeh, S. H., and Wei, Y. H. 1989. Liver mitochondrial respiratory functions decline with age. Biochemical and Biophysical Research Communications 165:944–1003.
39. Yen, T. C., King, K. L., Lee, H. C., Yeh, S. H., and Wei, Y. H. 1994. Age-dependent increase of mitochondrial DNA deletions together with lipid peroxides and superoxide dismutase in human liver mitochondria. Free Radical Biology and Medicine 16(2):207–214.
40. Soong, N W, Amnheim, N. Detection and quantification of mitochondrial DNA deletions. Methods Enzymol. 1996;264:421–31.
41. Lee C M, Weindruch R, Aiken J M. Age-associated alterations of the mitochondrial genome. Free Radic. Biol. Med. 1997;22(7):1259–69.
42. Zhang, C., Baumer, A., Maxwell, R. J., Linnane, A. W., and Nagley, P. 1992. Multiple mitochondrial DNA deletions in an elderly human individual. FEBS Letters 297:4–8.
43. Hamblet and Castora, Mitochondrial DNA deletion analysis: a comparison of PCR quantitative methods. Biochem Biophys Res Commun. 1995 15;207(2):839–47.
44. Yen, T. C., Pang, C. Y., Hsieh, R. H., Su, C. H., King, K. L., and Wei, Y. H. 1992. Age-dependent 6 kb deletion in human liver mitochondrial DNA. Biochemistry International 26:457–468.
45. Lezza, A. M., Boffoli, D., Scacco, S., Cantatore, P., and Gadaleta, M. N., 1994, Correlation between mitochondrial DNA 4977-bp deletion and respiratory chain enzyme activities in aging human skeletal muscles Biochemical and Biophysical Research Communications 205:772–779.
46. Yang, J. H., Lee, H. C., Lin, K. J., and Wei, Y. H., 1994. A specific 4977-bp deletion of mitochondrial DNA in human ageing skin, Archives of Dermatological Research 286: 386–390.
47. Yen, T. C., King, K. L., Lee, H. C., Yeh, S. H., and Wei, Y. H., 1994, Age-dependent increase of mitochondrial DNA deletions together with lipid peroxides and superoxide dismutase in human liver mitochondria, Free Radical Biology and Medicine, 16: 207–214.
48. Lee, H. C., Pang, C. Y., Hsu, H. S., and Wei, Y. H., 1994, Differential accumulations of 4,977 bp deletion in mitochondrial DNA of various tissues in human ageing, Biochimica et Biophysica Acta, 1226: 37–43.
49. Wei, Y. H., 1992, Mitochondrial DNA alterations as ageing-associated molecular events. Mutation Research 275: 145–155.
50. Yen, T. C., Pang, C. Y., Hsieh, R. H., Su, C. H., King, K. L., and Wei, Y. H., 1992, Age-dependent 6 kb deletion in human liver mitochondrial DNA, Biochemistry International 26: 457–468.
51. Taanman J W., The mitochondrial genome: structure, transcription, translation and replication., Biochim. Biophys. Acta, 1999, 1410:103–23.

Any patents or publications mentioned in this specification are indicative of the level of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

I claim:

1. A method of obtaining a measurement indicative of oxidative stress in an individual subject, the method comprising the steps of:
   a) obtaining a specimen from an individual, wherein the obtaining a specimen does not include obtaining a specimen by organ biopsy;
   b) performing an assay on the specimen to detect a quantity of a mitochondrial DNA deletion;
   c) comparing the quantity of the deletion to a reference to obtain a first value;
   d) making a quantitative measurement of a parameter related to oxygen metabolism in the individual to obtain a second value wherein the parameter related to oxygen metabolism is selected from the group consisting of: breathing rate, respiratory quotient, heart rate, basal metabolic rate, caloric intake, and calculating caloric expenditure; and
   e) relating the first and second values to obtain a measurement indicative of oxidative stress.

2. The method of claim 1, wherein the assay to detect a mitochondrial DNA deletion is selected from the group consisting of: polymerase chain reaction, primer extension, restriction fragment length polymorphism, in situ hybridization, reverse transcription-PCR, differential display of RNA, and antibody-based protein detection.

3. The method of claim 1, wherein the reference is selected from the group consisting of: non-deleted mitochondrial DNA, genomic DNA, RNA and protein.

4. The method of claim 1, wherein the specimen is cells selected from the group consisting of: epidermal, mucosal, epithelial, hair root, spermatozoa and blood.

5. The method of claim 1, wherein the first value varies in the time period over which the value is measured relative to the second value.

6. The method of claim 1, further comprising the step of comparing the first value to an external standard to obtain a second measurement of oxidative stress.

7. The method of claim 6 wherein the external standard is a measurement of a mitochondrial DNA deletion in a second individual.

8. The method of claim 6 wherein the external standard is a plurality of measurements of a mitochondrial DNA deletion in a plurality of individuals, the plurality of individuals characterized by ages ranging from 0–120 years.

* * * * *